US012642762B2

(12) United States Patent
Ward et al.

(10) Patent No.: US 12,642,762 B2
(45) **Date of Patent: *Jun. 2, 2026**

(54) ALLERGENIC PROTEIN FORMULATIONS FOR IMMUNOTHERAPY

(71) Applicant: CAMBRIDGE ALLERGY LIMITED, Cambridgeshire (GB)

(72) Inventors: Robert Neil Ward, Deeside (GB); Ryan John Anthony Wilson, Deeside (GB); Michael John Frodsham, Deeside (GB)

(73) Assignee: CAMBRIDGE ALLERGY LIMITED, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/629,431

(22) Filed: Apr. 8, 2024

(65) Prior Publication Data

US 2024/0252430 A1 Aug. 1, 2024

Related U.S. Application Data

(63) Continuation of application No. 16/761,491, filed as application No. PCT/EP2018/080159 on Nov. 5, 2018, now Pat. No. 11,980,684.

(30) Foreign Application Priority Data

Nov. 6, 2017 (GB) ..................................... 1718342

(51) Int. Cl.
| | |
|---|---|
| *A61K 9/00* | (2006.01) |
| *A61K 9/16* | (2006.01) |
| *A61K 9/48* | (2006.01) |
| *A61K 39/35* | (2006.01) |

(52) U.S. Cl.
CPC .......... *A61K 9/0053* (2013.01); *A61K 9/1652* (2013.01); *A61K 9/4858* (2013.01); *A61K 39/35* (2013.01)

(58) Field of Classification Search
None
See application file for complete search history.

(56) References Cited

U.S. PATENT DOCUMENTS

| | | | |
|---|---|---|---|
| 2006/0269576 A1 | 11/2006 | Moldt et al. | |
| 2014/0271836 A1* | 9/2014 | Walser | A61P 37/06 424/452 |
| 2015/0343075 A1* | 12/2015 | Raff | A61K 9/4866 514/783 |
| 2017/0021010 A1* | 1/2017 | Erstein | B65D 75/527 |

FOREIGN PATENT DOCUMENTS

| | | | |
|---|---|---|---|
| CN | 101496902 A * | 8/2009 | |
| WO | WO 2013/173697 A1 | 11/2013 | |
| WO | WO-2016020336 A1 * | 2/2016 | A61K 39/35 |

OTHER PUBLICATIONS

International Search Report and Written Opinion from parent PCT Application No. PCT/EP2018/080159, 13 pages (mailed Jul. 23, 2019).

* cited by examiner

*Primary Examiner* — Susan T Tran
(74) *Attorney, Agent, or Firm* — KLARQUIST SPARKMAN, LLP

(57) ABSTRACT

This invention relates to an oral immunotherapy (OIT) composition comprising granules that contain an allergenic protein, such as peanut protein, along with a humectant, such as trehalose, and a binder, such as hypromellose. The composition may further comprise a filler, such as mannitol and a lubricant, such as stearic acid. OIT compositions, methods of preparing OIT compositions and methods of treatment of food allergy using OIT compositions are provided.

23 Claims, 1 Drawing Sheet

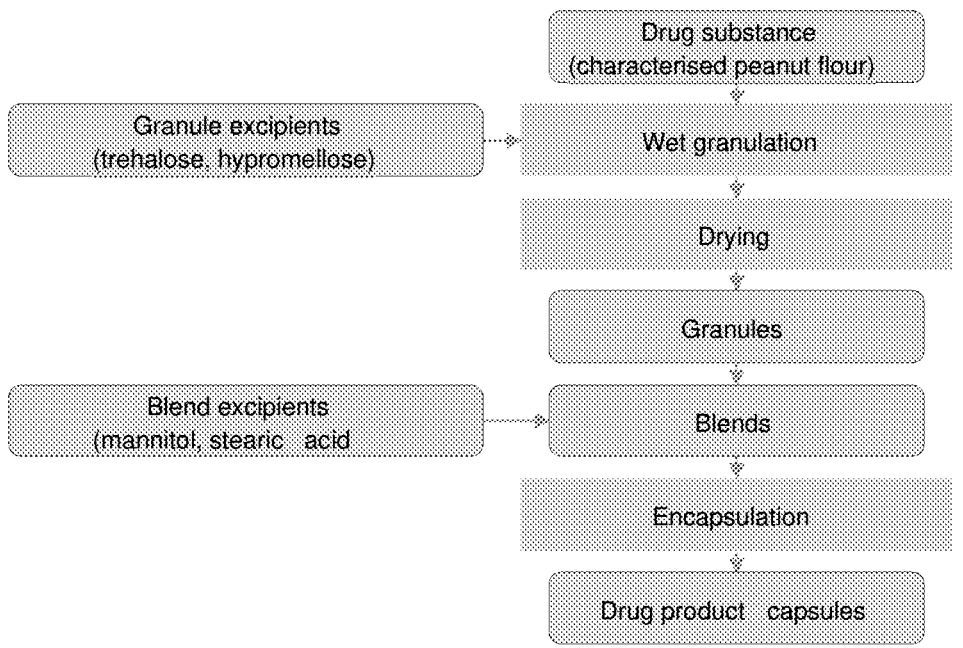

ALLERGENIC PROTEIN FORMULATIONS FOR IMMUNOTHERAPY

CROSS REFERENCE TO RELATED APPLICATIONS

This application is a continuation of U.S. application Ser. No. 16/761,491, filed May 4, 2020, which is the U.S. National Stage of International Application No. PCT/EP2018/080159, filed on Nov. 5, 2018, which was published in English under PCT Article 21(2), which in turn claims the benefit of Application No. GB1718342.7, filed on Nov. 6, 2017, which is incorporated herein by reference in its entirety.

FIELD

The present invention relates to formulations of allergenic proteins and particularly, although not exclusively, to peanut protein formulations, for example for use in oral immunotherapy.

BACKGROUND

Peanut allergy is common, affecting 1-2% of young children in Europe and the USA [1-3], and unlike other common childhood food allergies (e.g. to hen's egg), resolution is uncommon [4]. The quality of life of the affected families is reduced because of constant fear over food choices and the likelihood of anaphylaxis [5, 6]. Despite the current best management, families of peanut allergic children have poor knowledge of how to avoid and also treat food allergy emergencies [7]. Accidental reactions are common (annual incidence rates for accidental reactions of 3, 14, and 50% have been reported in large studies [8]) Nearly one third of nut-allergic children cannot recognise the nut to which they are allergic—this lack of recognition puts them at increased risk of unintentional ingestion [9]. There is therefore a need to develop a disease-modifying therapy for peanut allergy.

Immunotherapy for inhalant and stinging insect allergy by subcutaneous injection has proven efficacy and safety. An early study of subcutaneous immunotherapy for peanut allergy showed a trend to benefit but was terminated after a severe adverse reaction [10]. Oral immunotherapy (OIT) for the treatment of persistent hen's egg and cow's milk allergy has been studied [11, 12]. Sublingual immunotherapy with hazelnut extract was studied in a small group of subjects with hazelnut allergy demonstrating an increase in dose threshold [13]. Two recently published studies of peanut oral immunotherapy employing an initial rush protocol showed poor tolerability of the rush period, with better efficacy after a period of gradual dose escalation [14-16]. Small trials of peanut oral immunotherapy using an initial dose matched to the patient's challenge threshold and gradual dose escalation has previously been reported [17, 21].

Formulations of allergenic proteins for the wide-spread use of OIT to treat peanut and other food allergies have particular requirements. The stability of the allergenic protein needs to be maintained across a range of protein concentrations or doses, the formulation needs to support the accurate and consistent measurement of the total and individual amounts of allergenic protein and also to retain the potency of the immunogenic effect of the allergenic protein. In addition, the formulation should mask the taste of the allergenic protein, so the composition is palatable to allergy patients with an aversion to it. Aversion to the taste of peanut is highly prevalent amongst the target population and leads to reduced compliance with regular dosing and hence overall lower efficacy of the drug. Successful taste masking to improve palatability should contribute to greater efficacy. The production of suitable formulations is challenging.

SUMMARY

The present inventors have developed a formulation for allergenic proteins that offers significant advantages in oral immunotherapy for the treatment of food allergies.

An aspect of the invention provides an oral immunotherapy (OIT) composition comprising or consisting of;
- (i) granules comprising allergenic protein, a humectant and a binder
- (ii) filler; and
- (iii) lubricant In a preferred embodiment, the oral immunotherapy (OIT) composition may comprise or consist of;
- (iv) granules comprising allergenic protein, trehalose and hypromellose,
- (v) mannitol; and
- (vi) stearic acid.

The allergenic protein may be a food allergen, preferably peanut protein.

Another aspect of the invention provides a set of unit dose formulations of an OIT composition. The set may include unit dose formulations comprising one or more of 2, 5, 12.5, 25, 50, 100, 200 and optionally 400 mg allergenic protein.

Another aspect of the invention provides an OIT composition as described herein for use in the treatment of the human or animal body.

Another aspect of the invention provides an OIT composition as described herein for use in the treatment of food allergy, preferably peanut allergy.

Another aspect of the invention provides a method of treatment of a food allergy, preferably peanut allergy, comprising administering an OIT composition as described herein to an individual in need thereof.

Another aspect of the invention provides a method of producing an OIT composition comprising
- (vii) producing granules comprising an allergenic protein, disaccharide and a binder; and
- (viii) blending the granules with filler and a lubricant to produce the OIT composition.

The OIT composition may be further formulated, for example by filling into a sachet or drinking straw, encapsulation into a capsule or compression into a tablet.

The invention includes the combination of the aspects and preferred features described except where such a combination is clearly impermissible or expressly avoided.

BRIEF DESCRIPTION OF THE FIGURES

FIG. 1 shows a schematic representation of an example of a production process for an OIT composition.

DETAILED DESCRIPTION

This invention relates to an oral immunotherapy (OIT) composition comprising or consisting of (i) granules comprising allergenic protein, humectant and a binder, (ii) filler and (iii) lubricant. The presence of the humectant in the granules may facilitate the maintenance of low water activity and OIT compositions described herein are able to maintain the stability and potency of the allergenic protein across a range of doses, in addition to allowing the precise detection of the presence and potency of the allergenic protein by analytical tests. The flow properties of the granules provide a high degree of uniformity of unit dosage formulations, even when the granules are heavily diluted at low dosages (for example 2 mg or 5 mg) in large dose forms (for example, size 0 or 00 capsules).

OIT compositions as described herein may also mask the taste of the allergenic protein, making it palatable to allergy patients. The OIT compositions may also display favourable physical properties and may be formulated into capsules and tablets without the need for glidants or anti-caking agents. The OIT composition may also be compatible with analytical techniques used in pharmaceutical testing, The OIT compositions described herein comprise granules of allergenic protein, humectant and a binder.

The presence in the OIT compositions of granules comprising the allergenic protein and humectant allows the accurate and uniform formulation of the composition at low dose strengths. The concentration of the allergenic protein in the granule is reduced by the presence of the humectant and the granule concentration within the bulk composition is reduced by the presence of the filler. This double dilution improves dose accuracy and consistency at low dose strengths. The granules also provide the composition with flow properties that allow efficient production.

An OIT composition may comprise 4% (w/w) to 100% (w/w) granules, preferably 10% (w/w) to 95% (w/w) or 20% (w/w) to 90% (w/w). The granules in the OIT composition may comprise 5% to 95% (w/w) allergenic flour, 2% to 85% (w/w) humectant and 2% to 25%, preferably 2% to 3% (w/w) binder.

An allergenic protein is a protein antigen capable of inducing an allergic response in a mammalian subject, preferably a human subject. Allergenic proteins may include plant proteins, such as peanut protein, tree nut protein, soy protein, wheat protein, fruit protein, mustard protein, and celery protein, sesame seed protein, and animal proteins, such as fish protein, shell fish protein, galactose-alpha-1, 3-galactose (alpha-gal), egg protein, beef protein, pork protein, and cow's milk protein.

In preferred embodiments, the allergenic protein may be peanut protein, such as Ara h1, Ara h2, Ara h3, Ara h6, Ara h8 and Ara h9 and combinations of some or all of these proteins.

In some embodiments, the granules may be formulated into batches containing discrete amounts of allergenic protein, for example 5% (w/w), 12% (w/w), 25% (w/w) and/or 95% (w/w). This allows the amount of allergenic protein in the OIT composition to be conveniently adjusted during formulation by altering the amount or the batch of granules in the composition. This is useful in providing a range of different doses of allergenic protein using the compositions described herein.

The amount of allergenic protein in the OIT composition depends on the desired dose that is to be administered to a subject. Typically an OIT composition may comprise 0.3% to 50% (w/w) allergenic protein or 0.5% to 40% (w/w) allergenic protein.

Conveniently, the allergenic protein may be comprised in a dried powder, such as flour, freeze-dried milk, egg powder or animal protein powder. A suitable powder may be generated from a natural source that contains the allergenic protein. In some embodiments, a defatting or drying or desiccating step may be employed. For example, a flour may be obtained by grinding raw nuts, grains or roots that contain the allergenic protein, such as peanuts or tree nuts. Dried powders, such as flours, may be produced by conventional techniques or obtained from commercial suppliers. A dried powder, such as a flour, may for example comprise 25% to 60%, 30% to 55% or 35% to 45% allergenic protein. In preferred some embodiments, the allergenic flour may be peanut flour. A peanut flour may for example comprise 35% to 55% peanut protein, for example 38% to 44% peanut protein.

The amount of allergenic flour in the OIT composition depends on the desired dose of allergenic protein that is to be administered to a subject. Typically an OIT composition may comprise 1% (w/w) to 95% (w/w) allergenic flour.

A humectant is a hygroscopic excipient that facilitates the retention of moisture in a composition and prevents desiccation. The presence of the humectant allows the granules to retain bound water after drying, for example at 50-65° C. For example, the granules may retain about 1% to 10% or 2% to 9% bound water. This bound water may be released from the granules by heating to 105° C., for example during a loss on drying test. The humectant may also be useful in sweetening the OIT composition and facilitating disintegration. An OIT composition may comprise 0.5% to 95% (w/w) humectant for example, 0.5% to 50% (w/w), preferably 1% to 45% (w/w).

Suitable humectants include sugar alcohols, such as xylitol, maltitol, inositol, sorbitol and erythritol; polysaccharides, such as starch and polydextrose; monosaccharides, such as tagatose; and disaccharides, such as sucrose, lactose, maltose and trehalose.

Preferably, the humectant is a disaccharide, most preferably trehalose. Trehalose is a naturally occurring disaccharide comprising two α-glucose units linked by an α, α-1, 1-glucoside bond. In some preferred embodiments, trehalose may be in a hydrated form, such as trehalose dihydrate. In some embodiments, the composition may lack anhydrous forms of trehalose. The composition may comprise 0.1% to 50% (w/w) trehalose, preferably 0.5% to 45% (w/w).

A binder is an excipient that facilitates the agglomeration of powder into granules during mixing with solvents (i.e. wet granulation). An OIT composition may comprise 0.01% (w/w) to 25% (w/w) binder, for example 0.1% (w/w) to 5% (w/w) binder. In some embodiments a delayed release formulation may comprise up to 80% (w/w) binder. Suitable binders are well known in the art (see for example US Pharmacopeia 40 National Formulary 35) and include povidone, copovidone, ethylcellulose, gelatin, hydroxyethyl cellulose, hydroxypropyl cellulose, methylcellulose, polycarbophil, polyvinyl acetate, and hypromellose. In preferred embodiments, the binder is hypromellose.

A filler or diluent is an excipient that is incorporated into dosage forms to increase volume or weight of the dosage form. Preferably the filler has a particle size that is similar to the granules. An OIT composition may comprise 5% (w/w) to 95% (w/w) filler. Fillers with a range of particle sizes are commercially available. Suitable fillers are well known in the art and include amino methacrylate, copolymer calcium carbonate, magnesium oxide, magnesium carbonate, simethicone, sodium chloride and mannitol. In preferred embodiments, the filler is mannitol.

A lubricant is an excipient that reduces friction between the particles of a composition and between the particles of the composition and manufacturing equipment surfaces during the manufacture of solid dosage forms of the composition, for example, during encapsulation or tablet compression. The lubricant is typically added in the last step of formulation, so it is able to move freely around the powder without being bound into the granule.

An OIT composition may comprise 0.5% (w/w) to 10% (w/w) lubricant, for example 0.5% (w/w) to 5% (w/w) or 0.5% (w/w) to 3% (w/w), Suitable lubricants for use in the OIT compositions described herein are well known in the art (see for example USP 40 NF 35) include talc, magnesium stearate, stearic acid, sodium stearyl fumarate, sodium lauryl sulphate and hydrogenated vegetable oil. Preferably, the lubricant is stearic acid.

Preferably, an OIT composition described herein does not contain glidants or anti-caking agents. Glidants and anti-caking agents are used to promote powder flow and to reduce the caking or clumping that can occur when powders are stored in bulk. An OIT composition may be in a form that is suitable for oral administration. For example, the composition may be suitable for admixing with a foodstuff, such as yoghurt.

Suitable humectants, binders, fillers and lubricants as described above can be found in standard pharmaceutical texts, for example, Remington's Pharmaceutical Sciences, 18th edition, Mack Publishing Company, Easton, Pa., 1990 and US Pharmacopeia 40-NF 35 and are available from commercial suppliers.

The OIT composition will generally be in a unit dose form i.e. the OIT composition is distributed into units, each of which contains a defined dose of the allergenic protein. The amount of allergenic protein in the unit dose form is determined by the OIT regimen in which the composition is employed. Suitable regimens are well-known in the art (see for example, Agnostou et al Lancet. 2014 Apr 12; 383 (9925):1297-304; WO2012/123759). For example, a unit dose form of an OIT composition described herein may contain 2, 5, 12.5, 25, 50, 100, 200 mg, 400 mg, 800 mg or 1000 mg of allergenic protein, such as peanut protein, preferably 2, 5, 12.5, 25, 50, 100 or 200 mg allergenic protein.

A unit dose of an OIT composition described herein may comprise 20 mg to 5000 mg, preferably 40 mg to 550 mg of granules comprising allergenic protein, disaccharide and a binder. For example, the unit dose may comprise 5 mg to 500 mg allergenic flour, 3 mg to 180 mg disaccharide and 0.5 mg to 125 mg, preferably 0.5 mg to 16 mg binder. A unit dose of an OIT composition described herein may further comprise 30 mg to 420 mg filler and 1 to 6 mg lubricant.

An OIT composition as described herein may be provided as a set of unit dose formulations. The unit dose formulations of the OIT composition may be provided in any convenient form, for example in capsules, sprinkle capsules, sachets, tablets or suspensions. Suitable methods for formulating compositions into capsules, sprinkle capsules, sachets, tablets and suspensions are well known in the art.

The set may comprise unit dose formulations containing different amounts of allergenic protein, as determined by an OIT regimen. For example, the set may comprise unit dose formulations containing 2 mg, 5 mg, 12.5 mg, 25 mg, 50 mg, 100 mg, 200 mg and optionally 400 mg allergenic protein.

A set of unit dose formulations may further comprise one or more placebo formulations. Suitable placebo formulations may consist of an OIT composition as described herein with colourants, flavours and/or odorants instead of the allergenic protein.

The unit dose formulations may be separately packaged in sealed units, for example to protect the contents from the external environment. The unit dose formulations may be packaged in separate sealed containers, for example wrappers, pouches, bags, cartons, capsules, sachets, vials or tubes.

The set may comprise 5 or more, 10 or more, 14 or more, 15 or more, 20 or more, 25 or more, 30 or more or 35 or more unit dose formulations. In some embodiments, the set may comprise unit dose formulations sufficient for two, three or four weeks administration, for example, 14, 21 or 28 unit dose formulations.

In some embodiments, OIT compositions described herein may be administered directly to a subject (i.e. without admixing with a foodstuff). In other embodiments, OIT compositions may be admixed with a foodstuff before administration. For example, a unit dose of an OIT composition may be admixed with a foodstuff and the foodstuff then ingested by the subject. Suitable foodstuffs include dairy or dairy substitute products, such as yoghurt, milkshake or chocolate, or another food product with similar properties, cooked or baked food products, such as biscuits or cake; confectionery (e.g. chocolate, sweets and jellies) and beverages. Dairy substitute products may include soy-based products.

Another aspect of the invention provides an OIT composition as described herein for use in the treatment of food allergy. The type of food allergy will determine the allergenic protein that is included the OIT composition. For example, OIT compositions may be useful in the treatment of plant allergies, such as peanut allergy, tree nut allergy, soy allergy, wheat allergy, fruit allergy, corn allergy and garlic allergy, and animal allergies, such as fish allergy, shell fish allergy, galactose-alpha-1, 3-galactose (alpha-gal) allergy, egg allergy, and milk allergy. Preferably, the allergenic protein is peanut protein and the OIT composition is used for the treatment of peanut allergy.

OIT composition as described herein may be produced using formulation processes that are well-known in the art. For example, as an initial step, the allergenic protein content of a flour or other extract containing allergenic protein may be determined. Suitable methods for characterising protein content are well-known in the art and include RP-HLPC and LC-MS/MS. The flour or other powder containing the allergenic protein may be admixed with the humectant in a granulator. The mixture may then be admixed with an aqueous granulation solution comprising the binder and agitated, for example using an impeller, screws, or air, in a wet granulation process. Agitation of the mixture in the granulation solution in the presence of the binder causes particles of the mixture to coalesce to produce wet granules. The wet granules may then be dried, for example by heating to 50 to 70° C., preferably about 65° C., to remove the aqueous granulation solution, leaving dry granules of flour and disaccharide bound together with the binder. Suitable wet granulation techniques are well-known in the art. After drying, the granules may be blended with filler and a lubricant using standard blending techniques to generate the OIT composition. The OIT composition may then be distributed into unit dose formulations, for example by encapsulating into capsules or compressing into tablets, using standard techniques. Dose formulations may be tested using analytical techniques to confirm the purity and allergenic protein content and subsequently packaged, for example in a blister pack.

% (w/w) as used herein refers to the mass fraction which may be defined as the ratio of the mass of one component $m_c$ of the composition to the total mass of the all the components in the composition $m_t$, where % (w/w)=$m_c/m_t$×100.

Other aspects and embodiments of the invention provide the aspects and embodiments described above with the term "comprising" replaced by the term "consisting of" and the aspects and embodiments described above with the term "comprising" replaced by the term "consisting essentially of".

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such, these are within the scope of the present invention.

All documents and sequence database entries mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

EXPERIMENTAL

Example 1-Stability of Dose Formulations

Ara h1, Ara h2, Ara h3 and Ara h6 proteins in peanut flour were analysed by LC-MS/MS. Trehalose and microcrystalline Cellulose (Avicel™) were compared as excipients in peanut flour formulations. The formulations A-D were prepared as shown in Tables 1-3 below.

TABLE 1

| Formulation | Dose (mg protein) | Batch Number | Protocol Number | Excipient |
|---|---|---|---|---|
| A | 2 | CUH002/027A1 | SF/15/0007 | Trehalose |
|  | 5 | CUH002/027A2 | SF/15/0008 | Trehalose |
| B | 2 | CUH002/018A1 | SF/15/0009 | Avicel |
|  | 5 | CUH002/018A2 | SF/15/0010 | Avicel |
| C | 2 | CUH002/021A1 | SF/15/0012 | Trehalose |
|  | 12.5 | CUH002/021A2 | SF/15/0013 | Trehalose |
|  | 50 | CUH002/021A3 | SF/15/0014 | Trehalose |
|  | 200 | CUH002/021A4 | SF/15/0015 | Trehalose |
| D | 2 | CUH002/024A1 | SF/15/0016 | Avicel |
|  | 12.5 | CUH002/024A2 | SF/15/0017 | Avicel |
|  | 50 | CUH002/024A3 | SF/15/0018 | Avicel |
|  | 200 | CUH002/024A4 | SF/15/0019 | Avicel |

60

TABLE 2

| FORMULATION | Batch Ref | Peanut Flour | Trehalose | Avicel PH301 | PVP |
|---|---|---|---|---|---|
| A | CUH002/027A | 10 | 87 | N/A | 3 |
| B | CUH002/018A | 10 | N/A | 87 | 3 |
| C | CUH002/021A | 80 | 17 | N/A | 3 |
| D | CUH002/024A | 80 | N/A | 15 | 5 |

TABLE 3

FORMULATION A

| Batch Ref | Peanut Flour Dose (mg) | PF Granule used-CUH002/027A PF Granule | Mannitol | Magnesium Stearate |
|---|---|---|---|---|
| CUH002/027A1 | 2 | 27.6 | 71.4 | 1 |
| CUH002/027A2 | 5 | 68.1 | 30.9 | 1 |

FORMULATION B

| Batch Ref | Peanut Flour Dose (mg) | PF Granule used-CUH002/018A PF Granule | Mannitol | Magnesium Stearate |
|---|---|---|---|---|
| CUH002/018A1 | 2 | 27.6 | 71.4 | 1 |
| CUH002/018A2 | 5 | 68.1 | 30.9 | 1 |

FORMULATION C

| Batch Ref | Peanut Flour Dose (mg) | PF Granule used-CUH002/021A PF Granule | Mannitol | Magnesium Stearate |
|---|---|---|---|---|
| CUH002/021A1 | 2 | 3.5 | 95.5 | 1 |
| CUH002/021A2 | 12.5 | 22 | 77 | 1 |
| CUH002/021A3 | 50 | 50.3 | 48.7 | 1 |
| CUH002/021A4 | 200 | 79.2 | 19.8 | 1 |

FORMULATION D

| Batch Ref | Peanut Flour Dose (mg) | PF Granule used-CUH002/024A PF Granule | Mannitol | Magnesium Stearate |
|---|---|---|---|---|
| CUH002/024A1 | 2 | 3.5 | 95.5 | 1 |
| CUH002/024A2 | 12.5 | 21.9 | 77.1 | 1 |
| CUH002/024A3 | 50 | 50.3 | 48.8 | 1 |
| CUH002/024A4 | 200 | 78.9 | 20.1 | 1 |

Methods

Formulation

Deionised water for the primary granulation fluid was dispensed into a stock solution vessel. The required amount of HPMC E3 was dispensed into a suitable sized duma using a 3 place balance. The water was stirred with an overhead stirrer so as to create a vortex and the HPMC slowly added. Stirring continued until a homogeneous solution is formed, then the beaker was covered to prevent evaporation.

The required amount of peanut flour for one sub-lot was dispensed into a vessel using a 3 place balance. The peanut flour was passed through a 1.0 mm sieve into a stainless steel collection vessel. The flour was transferred to the bowl of a Multi Pro™ mixer. The required amount of trehalose or microcrystalline cellulose (Avicel™) for one sub-lot was dispensed into a suitable sized vessel using a 3 place balance. The trehalose or microcrystalline cellulose was passed through a 1.0 mm sieve into the same stainless steel collection vessel as the flour. The trehalose was transferred to the bowl of the mixer, the lid closed and the mixer started at a speed setting of 2-4 for 1 minute. The flour and trehalose were mixed until the blend was homogeneous.

The required amount of the primary granulation fluid for one sub-lot was transferred into a dispensing vessel. The blend of flour and trehalose/microcrystalline cellulose was mixed in the mixer at a speed setting of 2-4 and the primary granulation fluid added gradually at a steady rate over the course of 5 minute. The resultant granules were passed through a 2.0 mm sieve into a stainless steel collection vessel. The granules were poured into a large stain less steel tray, and dried in an oven set to 65° C. for at least 12 hours. The trays were then removed and the dried granules stored in a sealed container to prevent uptake of moisture from the atmosphere.

The dried granules were milled using a Comil™ mill with a1270 μm screen and a round bladed impeller set at @ 33 HZ/2000 RPM. The milled granules were collected in polythene bags tied to the outlet of the mill. The milled material was passed through a 500 μm mesh into a steel collection pan and collected and subjected to bulk density and other analytical tests.

The required amounts of granules and mannitol (Mammogem™ Granular) were dispensed into a container. Lubricant (talc or stearic acid) was sieved through a 250 μm mesh and added to the container and blended at 30 rpm for 5 minutes using an Erweka AR401 granulator until the blend was homogeneous.

A Profiller™ 1100 was set for Size 0 capsules. The Profiller 1100 was loaded with capsules and the blend poured onto the centre of capsule filling tray and spread over the capsules, such that all capsules received the same amount of blend. The tray containing the capsule lids was replaced over the filled capsules and pressed until the capsules fully closed. This was repeated until the required number of capsules was obtained.

Ara h Protein Levels Measured by LCMS

Levels of Ara h1, Ara h2 and Ara h6 in protein extracts were determined by matching test sample retention times of trypsinised fragments with known external fragment standards (Ara h1-13aa, Ara h2-9aa, Ara h6-12 aa) on a Sciex AS 4000 Quadrupole Mass Spectrometer attached to a Waters Aquity UPLC system.

Protein Extraction

Test sample of known peanut protein content was weighed using a suitable balance and proteins extracted using guanidine hydrochloride and ammonium bicarbonate solutions. A BCA total protein assay (Thermo Scientific™ Pierce™ BCA Protein Assay), based on protein in an alkaline solution driving the reduction of $Cut^{++}$ to $Cu^+$ (the biuret reaction) and 2 Cu+ ions binding one BCA molecule and producing a purple product detectable at 562 nm, was then performed on the resultant peanut extract to enable the LC-MS assay.

For each test sample 4 mL 6M guanidine hydrochloride was added and the sample vortexed before being sonicated to 10 minutes at room temperature and vortexed again. 16 mL 50 mM ammonium bicarbonate was then added, the mixture briefly vortexed before being sonicated for 10 minutes at room temperature and vortexed again. Finally, the sample was centrifuged at 2600 g for 10 minutes and the supernatant, the protein extract, decanted to a separate labelled container and stored until required at –80° C.

Preparation of Key Reagents

Surrogate matrix protein extract was prepared from coconut flour. Other buffers were also generated; 10 mM DL-DTT in 50 mM ammonium bicarbonate, 100 mM iodoacetamide in 50 mM ammonium bicarbonate, 0.1 mg/mL trypsin in 50 mM ammonium bicarbonate, 1% formic acid in water; mobile phase A (0.2% formic acid in acetonitrile), mobile phase B (0.2% formic acid in water), weak needle wash (10% acetonitrile in water), peptide buffer solution (20% methanol, 0.1% formic acid, 0.1% BSA in water).

A working internal standard (IS) of mixed peptide fragments was generated from peptides dissolved in peptide buffer diluted down to working concentrations in surrogate matrix; final concentrations were 1 mcg/mL Ara h 1 IS, 3 mcg/mL Ara h 2 IS, 1.5 mcg/mL Ara h 3 IS and 4.5 mcg/mL Ara h 6 IS. Eight linearity standards containing each of the Ara peptides and QC controls (high, medium and low) were prepared in surrogate matrix. Test samples were prepared as protein extracts as described above in section.

Sample Preparation

Test samples, surrogate matrix (for blank and zero), linearity standard or QC samples (50 mcL) were added to a low bind 96 well plate. With the exception of blank wells, working internal standard (25 mcL) was added to each well. The plate was covered and placed on a plate shaker at 1200 RPM for 5 minutes before the samples were reduced by the addition of 150 mcl 10 mM DTT in 50 mM ammonium bicarbonate. The plate was covered and placed on a plate shaker at 1200 RPM for 5 minutes before being transferred to a 60° C. incubator for an hour. The reduced state of proteins in the samples was fixed with 40 mcL 100 mM iodoacetamide in 50 mM ammonium bicarbonate, the plate was again covered and placed on a plate shaker at 1200 RPM for 5 minutes. The plate was stored in the dark for 30 minutes before being removed to the light for 30 minutes. Samples were trypsin-digested with 50 mcl 0.1 mg/mL trypsin in 50 mM ammonium bicarbonate, the plate was covered and shaken at 1200 rpm for 5 minutes before being placed in a 37° C. incubator overnight. The reaction was terminated by the addition of 50 mcL 1% formic acid in water and mixing on a plate shaker for 5 minutes at 1200 RPM. Finally plates were centrifuged at 2600 g for 5 minutes and samples analysed by LC-MS/MS.

Samples were assayed immediately after preparation (T=0) and after 4 weeks storage at 40° C. in 75% humidity.

Results

Protein levels in formulations A to D after preparation and after 4 weeks storage at 40° C. in 75% humidity are shown in Table 4.

TABLE 4

| Formulation | Dose (mg protein) | Protocol Number | Excipient | T = 0 % W/W | T = 4 week % W/W |
|---|---|---|---|---|---|
| A | 2 | SF/15/0007 | Trehalose | 5.23 | 2.46 |
| B | | SF/15/0009 | Avicel | 3.44 | 1.75 |
| C | | SF/15/0012 | Trehalose | 4.03 | 3.76 |
| D | | SF/15/0016 | Avicel | 4.42 | 2.71 |
| A | 5 | SF/15/0008 | Trehalose | 5.25 | — |
| B | | SF/15/0010 | Avicel | 3.81 | — |
| C | 12.5 | SF/15/0013 | Trehalose | 5.75 | — |
| D | | SF/15/0017 | Avicel | 4.78 | 4.22 |

TABLE 4-continued

| Formulation | Dose (mg protein) | Protocol Number | Excipient | T = 0 % W/W | T = 4 week % W/W |
|---|---|---|---|---|---|
| C | 50 | SF/15/0014 | Trehalose | 5.79 | 5.09 |
| D | | SF/15/0018 | Avicel | 5.42 | 4.05 |
| C | 200 | SF/15/0015 | Trehalose | 4.96 | — |
| D | | SF/15/0019 | Avicel | 4.58 | — |

At T=0, trehalose formulated samples returned consistently higher values for the peanut component proteins Ara h 1, 2 and 6 when compared to identically prepared samples formulated with microcrystalline cellulose (Table 4). This occurred at both T=0 and T=4 weeks indicating a consistent stability advantage in using trehalose as an excipient in preference to microcrystalline cellulose (Table 4).

Example 2-Allergenic Potency of Drug Product Formulations Measured by Peanut Specific IgE Competitive ELISA A competitive ELISA was performed to measure the potency of various peanut formulations

Methods

ELISA

The ELISA is based on coating peanut protein sample extract to a plate, then allowing any peanut specific IgE from pooled human serum containing IgE antibodies reactive with Ara h 1, 2, 3, 8 and 9 (Peanut IgE Positive Pooled Human Serum: PIPPHS) to bind to the coated peanut antigen on the plate, and detecting bound IgE with anti-IgE-alkaline phosphatase which converts pNPP to become detectable at 405 nm. Absorbance at 405 nm is proportional to the amount of peanut antigens in the test article extract.

Preparation of Key Reagents

ELISA coating antigen, reference standard, quality control and standard curve were each produced from protein extractions of peanut. ELISA reference standards were prepared from peanut flour mixed with appropriate amounts of excipient before being extracted. Peanut IgE Positive Pooled Human Serum (PIPPHS) was generated by pooling sera from peanut IgE positive people. The specific IgE content of the PIPPHS is shown in Table 5.

TABLE 5

| Allergen or allergen component | Concentration in pooled human serum (kU/l) |
|---|---|
| Total peanut | 132 |
| Ara h 1 | 38.3 |
| Ara h 2 | 74.4 |
| Ara h 3 | 15.6 |
| Ara h 8 | 5.86 |
| Ara h 9 | 0.28 |

Blocking buffer (5% FBS, 1% tween 20) was prepared in PBS and stored at 4° C. for up to a month. Washing buffer (1×PBS, 0.05% Tween 20) was prepared and stored at room temperature for up to a month.

Preparation of ELISA Plate

Coating antigen samples were prepared by adding coating antigen protein extract to 50 mM sodium carbonate/sodium bicarbonate pH 9.2 and allowing adherence to a Greiner high binding plate overnight at 4° C. or at room temperature for 2 hours. Plates were washed 3 times with washing buffer, before being blocked with blocking buffer for an hour at room temperature, and washed thrice more with washing buffer. Wells were finally emptied by flicking off and ready for sample loading.

ELISA Assay

PIPPHS was diluted 1:40 in blocking buffer and incubated for 12 hours at temperature 4° C. Diluted anti-human IgE-AP conjugate (1:500) was added to each well and the plate incubated for 4 hours at room temperature. The plate contents were discarded and the plate washed 3 times with wash buffer. pNPP substrate in TRIS buffer was added and the colour reaction allowed to develop for 15-30 minutes at room temperature before being stopped by the addition of 50 mCL 3M NaOH. Plates were read at absorbance wavelength 405 nm.

Results

The potencies of formulations A to D after preparation and after 4 weeks storage at 40° C. in 75% humidity are shown in Table 6.

TABLE 6

| Formulation | Dose (mg protein) | Protocol Number | Excipient | T = 0 % potency | T = 4 week % potency |
|---|---|---|---|---|---|
| A | 2 | SF/15/0007 | Trehalose | 92 | 74 |
| B | | SF/15/0009 | Avicel | 82 | 69 |
| C | | SF/15/0012 | Trehalose | 93 | 89 |
| D | | SF/15/0016 | Avicel | 95 | 79 |
| A | 5 | SF/15/0008 | Trehalose | 96 | 86 |
| B | | SF/15/0010 | Avicel | 93 | 86 |
| C | 12.5 | SF/15/0013 | Trehalose | 99 | — |
| D | | SF/15/0017 | Avicel | 104 | 99 |
| C | 50 | SF/15/0014 | Trehalose | 104 | 92 |
| D | | SF/15/0018 | Avicel | 91 | 83 |
| C | 200 | SF/15/0015 | Trehalose | 107 | 90 |
| D | | SF/15/0019 | Avicel | 96 | 87 |

Formulations containing trehalose were found to show greater potency at both T=0 and at extending stability testing at 4 weeks, across most doses tested than formulations comprising microcrystalline cellulose (Table 6).

Example 3-Content Uniformity

Content uniformity was measured by bicinchoninic acid assay (Smith et al (1985) *Anal. Biochem.* 150 (1): 76-85) to determine the total amount of protein in solution, following extraction of the peanut protein from drug product following 4 weeks of stability storage.

Results

TABLE 7

| Dose (mg protein) | Protocol number | Excipient | T = 0 | T = 0 | T = 4 | T = 4 | Mean | SD | % CV |
|---|---|---|---|---|---|---|---|---|---|
| 2 | SF/15/0007 | Trehalose | 97 | 97.2 | 99.3 | 96.4 | 97.3 | 8.6 | 8.9 |
| 2 | SF/15/0012 | | 91.9 | 81.4 | 111 | 104 | | | |
| 2 | SF/15/0009 | Avicel | 79.8 | 76.4 | 89.9 | 85.5 | 95.2 | 16.0 | 16.8 |
| 2 | SF/15/0016 | | 110 | N/A | 112 | 113 | | | |
| 5 | SF/15/0008 | Trehalose | 197 | 189 | 188 | 196 | 192.5 | 4.7 | 2.4 |
| 5 | SF/15/0010 | Avicel | 166 | 171 | 162 | 155 | 163.5 | 6.8 | 4.1 |

The bicinchoninic acid assay demonstrated that the recovery and detection of peanut protein at two dose strengths was markedly superior in trehalose formulations compared to Avicel formulations (Table 7). In addition, the precision of each set of results for trehalose was found to be superior to those from Avicel formulations as shown by the smaller standard deviation and % CVs for trehalose in comparison.

Example 4-Taste Masking

The taste masking of effect of G5 2 mg and G90 100 mg doses presented in yogurt was compared to placebo and plain peanut flour.

Method

Formulation A-E were as shown in Table 8 below.

TABLE 8

| ID | Sample |
|---|---|
| A | 2 mg G5 capsule CUH 001 |
| B | 100 mg G90 CUH 001 |
| C | 100 mg peanut flour |
| D | Placebo |
| E | Placebo |

Formulations A-E in Table 8 were mixed with a low fat Greek yoghurt carrier and sampled by a panel of 11 non peanut-allergic adults Single 5 ml taste, fresh spoon with each taste; no conferring was permitted. There was no priming with regards to flavours that might be encountered, except for yogurt. Panel members decided order of tasting at own discretion. The panel members answered Q1. 'Can you taste only yogurt? (Y/N)' and Q2 if not, what other flavours are present? (text)

Results

Responses to Q1 ('Can you taste only yogurt? (Y/N)') are shown in Table 9.

TABLE 9

| | | Q1 | |
|---|---|---|---|
| | | Yes | No |
| A | 2 mg G5 | 10 | 1 |
| B | 100 mg G90 | 7 | 4 |
| C | 100 mg flour | 1 | 10 |
| D | Placebo | 9 | 2 |
| E | placebo | 9 | 2 |

Q2 response from the tester who answered no to Q1, was 'slight taste of something, not sure what'. Q2 responses from testers who answered no to Q1 for samples B and C are shown in Tables 10 and 11, respectively.

TABLE 10

| Nutty aftertaste |
| --- |
| Nut (powdery/floury texture |
| and flavour) |
| Salty |
| Blank |

TABLE 11

| peanut |
| --- |
| peanut |
| peanut |
| peanut |
| peanut |
| burnt nut (powdery/floury |
| texture and flavour) |
| slight peanut flavour |
| sesame |
| lemon |
| blank |

Q2 responses from testers who answered no to Q1 for samples D and E are shown in Table 12.

TABLE 12

| Fizzy |
| --- |
| Fruit |
| lemon |
| blank |

The two testers who correctly identified nut in sample B also identified nut in Sample C, and had correct placebo responses. Neither identified peanut in sample A. The tester who reported a salty flavour in sample B also identified peanut in sample C and had correct placebo responses. The tester who responded with no to Q1 for sample B but left the description blank, also reported no to Q1 for sample C (also blank), but had one incorrect placebo response (false positive—blank). When considering sample B alone vs 2×placebo doses, $1/11$ testers correctly identified peanut in the G90 100 mg granules, which was similar to the frequency expected by guessing correctly by chance (3.7/11). Blinding in G90 100 mg granules was superior to peanut flour alone.

Successful taste masking of peanut was therefore achieved using two different doses and granule strengths.

Example 5-Taste Masking of Granules Containing Trehalose Compared to Placebo

Method

Preparation 1 active formulation and 2 placebos (randomly labelled A (active), B (placebo), C (placebo)) were mixed with a low fat Greek yoghurt carrier and sampled by a panel of non peanut-allergic adults.

Instructions to Volunteers

The instructions to the testers were as follows: (i) please taste samples A, B, C; (ii) order of tasting to be random (iii) eat the same amount of food form each sample and (iv) between each sample wash out mouth with water.

Results 3 out of 19 volunteers correctly identified peanut in the active sample and two negative placebos. 16 out of 19 volunteers incorrectly identified either peanut in the placebo or failed to recognise peanut in the active sample. $3/19$ was fewer than expected by chance ($6/19$), and confirms effective taste masking in our sample of volunteers.

Conclusions

Compared to microcrystalline cellulose, the presence of the humectant trehalose allows recovery and detection of larger amounts of both the key allergenic and total proteins across all doses. In addition, after 4 weeks of storage in accelerated stability conditions (40° C./75% relative humidity), trehalose allows greater recovery and detection of the major peanut allergens. Allergenic potency, measured by peanut-specific IgE competitive ELISA using sera from peanut-allergic patients, is significantly greater in samples extracted from doses formulated with trehalose compared to microcrystalline cellulose. In addition, trehalose is associated with excellent taste masking across the dose range, compared to peanut flour and placebo.

REFERENCES

A number of publications are cited above in order to more fully describe and disclose the invention and the state of the art to which the invention pertains. Full citations for these references are provided below. The entirety of each of these references is incorporated herein.

1. Grundy J, et al J Allergy Clin Immunol 2002; 110:784-9.
2. Sicherer S H, et al. J Allergy Clin Immunol 2003;112:1203-7.
3. Kanny G et al J Allergy Clin Immunol 2001;108:133-40.
4. Ho M H et al. J Allergy Clin Immunol 2008;121:731-6
5. Primeau M N et al. Clin Exp Allergy 2000;30:1135-43.
6. Avery N J et al. Ped Allergy Immunol 2003: 14: 378-382
7. Kapoor S et al Allergy 2004;59:185-91.
8. Clark A T, Ewan P W. J Allergy Clin Immunol 2008; 122:286.
9. Ferdman R M et al Ann Allergy Asthma Immunol 2006;97:73-7.
10. Oppenheimer J J et al. J Allergy Clin Immunol 1992;90:256
11. Buchanan A D et al J Allergy Clin Immunol 2007; 119:199-205.
12. Longo G et al J Allergy Clin Immunol 2008;121:343-7.
13. Enrique E et al Ann Allergy Asthma Immunol 2008; 100:283-4.
14. Jones S M et al J Allergy Clin Immunol. 2009;124: 292-300
15. Hofmann A M et al J Allergy Clin Immunol. 2009; 124:286-91,
16. Blumchen K et al J Allergy Clin Immunol 2010;126: 83-91.
17. Clark A T et al Allergy 2009;64:1218-20.
18. Taylor S L et al Clin Exp Allergy 2004;34:689-95.
19. Taylor S L et al Food Chem Toxicol 2010 Mar;48(3): 814-9
20. Pumphrey R S et al J Allergy Clin Immunol 2007; 119:1018-9
21. Anagnostou K et al Clin Exp Allergy 2011; 41: 1273-81

The invention claimed is:
1. An oral immunotherapy (OIT) composition comprising:

(i) granules comprising allergenic protein, humectant and a binder, wherein the allergenic protein is peanut protein and the humectant is sugar alcohol;

(ii) filler, wherein the filler is mannitol; and (iii) lubricant, wherein the lubricant is stearic acid or sodium stearyl fumarate; and wherein the OIT composition comprises, based on the total weight of the composition:

0.3% to 40% (w/w) allergenic protein,

30% (w/w) to 95% (w/w) of said granules,

5% (w/w) to 95% (w/w) of said filler, 0.5% (w/w) to 5% (w/w) of said lubricant, and 0.1% to 50% (w/w) sugar alcohol;

and wherein the OIT composition lacks glidants or anti-caking agents.

2. The OIT composition according to claim 1 wherein the peanut protein is Ara h1, Ara h2, Ara h3 or Ara h6 or a combination of two or more thereof.

3. The OIT composition according to claim 1, wherein the allergenic protein is comprised in an allergenic flour.

4. The OIT composition according to claim 1, comprising 0.1% (w/w) to 25% (w/w) binder.

5. The OIT composition according to claim 1, wherein the binder is hypromellose.

6. The OIT composition according to claim 1, wherein the composition is suitable for admixing with a foodstuff.

7. The OIT composition according to claim 1, wherein the composition is in a unit dose formulation.

8. The OIT composition according to claim 7 wherein the unit dose formulation is in a capsule, tablet or suspension.

9. The OIT composition according to claim 7, wherein each unit dose comprises 5 mg to 1000 mg of allergenic flour.

10. The OIT composition according to claim 7, wherein each unit dose comprises 2 mg, 5 mg, 12.5 mg, 25 mg, 50 mg, 100 mg, 200 mg or 400 mg allergenic protein.

11. The OIT composition according to claim 7, wherein each unit dose comprises 3 mg to 180 mg of humectant.

12. The OIT composition according to claim 7, wherein each unit dose comprises 0.6 to 125 mg hypromellose.

13. The OIT composition according to claim 7, wherein each unit dose comprises 30 mg to 420 mg of mannitol.

14. The OIT composition according to claim 7, wherein each unit dose comprises 1 mg to 6 mg of stearic acid.

15. A set of unit dose formulations comprising unit doses of the composition of claim 1, the unit dose formulations in the set comprising 2, 5, 12.5, 25, 50, 100 and 200 mg and optionally 400 mg allergenic protein.

16. A set according to claim 15 wherein the unit dose formulations are in a capsule, tablet, or suspension.

17. A kit comprising a set of unit dose formulations according to claim 15 and instructions for use.

18. A foodstuff admixed with an OIT composition according to claim 1.

19. A method of treatment of peanut allergy comprising administering an OIT composition according to claim 1 to an individual in need thereof.

20. A method of producing an OIT composition comprising providing dry granules comprising an allergenic protein, sugar alcohol and a binder; and blending the dry granules with a filler and a lubricant, wherein:

the allergenic protein is peanut protein, the filler is mannitol, the lubricant is stearic acid;

wherein the OIT composition comprises, based on the total weight of the composition:

0.3% to 40% (w/w) allergenic protein,

30% (w/w) to 95% (w/w) of said dry granules,

5% (w/w) to 95% (w/w) of said filler, 0.5% (w/w) to 5% (w/w) of said lubricant, and 0.1% to 50% (w/w) sugar alcohol; and wherein the OIT composition lacks glidants or anti-caking agents.

21. The method according to claim 20 wherein the dry granules are produced by a method comprising: admixing allergenic protein, sugar alcohol, and a binder in a high-shear mixer to produce granules, and drying the granules to produce the dry granules.

22. The method according to claim 20, further comprising encapsulating unit doses of said composition to produce capsules.

23. The method according to claim 20, further comprising compressing unit doses of said composition to produce tablets.

* * * * *